United States Patent
Hissink et al.

(10) Patent No.: US 8,309,137 B2
(45) Date of Patent: *Nov. 13, 2012

(54) DL-LACTIDE-ϵ-CAPROLACTONE COPOLYMERS

(75) Inventors: Catharina Everdina Hissink, Groningen (NL); Theodorus Adrianus Cornelius Flipsen, Groningen (NL); Hans Wicher Kuijper, Giekerk (NL); Rob Steendam, Groningen (NL)

(73) Assignee: Polyganics BV (NL)

(*) Notice: Subject to any disclaimer, the term of this patent is extended or adjusted under 35 U.S.C. 154(b) by 0 days.

This patent is subject to a terminal disclaimer.

(21) Appl. No.: 12/841,472

(22) Filed: Jul. 22, 2010

(65) Prior Publication Data
US 2010/0312340 A1 Dec. 9, 2010

Related U.S. Application Data

(63) Continuation of application No. 10/308,214, filed on Dec. 2, 2002, now Pat. No. 7,785,628.

(30) Foreign Application Priority Data

Feb. 6, 2002 (EP) ..................................... 02075481

(51) Int. Cl.
*A61K 9/14* (2006.01)
(52) U.S. Cl. ........................................................ 424/489
(58) Field of Classification Search ................... 424/489
See application file for complete search history.

(56) References Cited

U.S. PATENT DOCUMENTS

| 4,045,418 A | 8/1977 | Sinclair |
| 4,057,537 A | 11/1977 | Sinclair |
| 4,539,981 A | 9/1985 | Tunc |
| 6,290,982 B1 | 9/2001 | Seppälä et al. |
| 6,472,502 B1 | 10/2002 | Jurgens et al. |

FOREIGN PATENT DOCUMENTS

| EP | 1077073 | 2/2001 |
| JP | 08092359 | 9/1996 |
| JP | 10204378 | 8/1998 |
| WO | 92/04393 | 3/1992 |

OTHER PUBLICATIONS

English abstract and computer translation of JP 10-204378.
Perego and Vercellio, "Copolymers of L- and D, L-lactide with 6-caprolactone: synthesis and characterization," Makromol. Chem.,194:2463-2469 (1993).
den Dunnen, et al, Biological performance of a degradable poly(lactic acid-E-caprolactone) nerve guide: Influence of tube dimensions, Journal of Biomedical Materials Research, vol. 29, 757-766 (1995).
Zhihua et al., "Synthesis and Characterization of Biodegradable ÿ-caprolactone/d, l-lactide Copolymers," Chinese Journal of Applied Chemistry, 14(2):5-7 (1997) (English abstract included).

Primary Examiner — Zohreh Fay
(74) Attorney, Agent, or Firm — Banner & Witcoff, Ltd.

(57) ABSTRACT

The present invention relates to specific DL-lactide-ϵ-caprolactone copolymers and the application of these polymers in the production of biodegradable medical applications. According to the present invention a polymeric material comprising poly(DL-lactide-co-ϵ-caprolactone) is provided, which is obtained by the copolymerization of DL-lactide and ϵ-caprolactone, having a lactide content of 51-75 mol %, most preferably of 62-69 mol %.

20 Claims, 4 Drawing Sheets

DL-LACTIDE-ε-CAPROLACTONE COPOLYMERS

RELATED APPLICATIONS

This application is a continuation of U.S. application Ser. No. 10/308,214 and filed Dec. 2, 2002; which claims the benefit of EP patent application number 02075481.8 and filed Feb. 6, 2002 both of which are hereby incorporated by reference in their entireties.

FIELD OF THE INVENTION

The present invention relates to specific DL-lactide-ε-caprolactone copolymers and the application of these polymers in the production of biodegradable medical applications, such as artificial nerve guides.

BACKGROUND OF THE INVENTION

Poly(L-lactide-co-ε-caprolactone) and its use as material for medical applications has been studied extensively in the past. Grijpma et al. described the use of a semi-crystalline copolymer of L-lactide and ε-caprolactone (50/50) for bridging of peripheral nerve defects (Polymer Bulletin 25 (1991) 327). Den Dunnen et al. (J. Mat. Sci.: Mat. in Med. 4 (1993) 521-525), Aldini et al. (Biomaterials 17 (1996) 959-962) and Rodriquez et al. (Biomaterials 20 (1999) 1489-1500) reported that poly(L-lactide-ε-caprolactone) was highly biocompatible and that the use of poly(L-lactide-co-ε-caprolactone) nerve guides resulted in good functional nerve recovery. However, it was concluded that the low degradation rate of the polymer (after two years a significant amount of biomaterial fragments was still present) made this material unsuitable for application in biodegradable nerve guides for clinical purposes (Den Dunnen et al. (Microsurgery, 14 (1993) 508-515)). The long-lasting presence of slow-degrading biomaterial fragments could negatively affect the nerve function.

In order to increase the degradation rate and lower the risk of the formation of long-lasting biomaterial fragments, Den Dunnen et al. decided to use poly(DL-lactide-ε-caprolactone) as the material of choice (J. Biomed. Mater. Res. 29 (1995) 757-766 and Microsurgery 17 (1997) 348-357). In these publications, nerve guides are disclosed, which are based on a copolymer having a 50:50 DL-lactide:ε-caprolactone ratio. Although significant improvement was obtained with regard to the degradation rate (Den Dunnen et al. reported that the material was completely resorbed after 12 months (J. Biomed. Mater. Sci. 36 (1997) 337-346)), the material is reported to suffer from some drawbacks, such as swelling during the degradation, which may hamper the nerve regeneration, in combination with a relatively fast decrease in mechanical strength (J. Biomed. Mater. Res. 51 (2000) 575-585).

It is an object of the present invention to provide a poly(DL-lactide-ε-caprolactone) material which shows improved behavior for biodegradable medical purposes for which both flexibility and mechanical strength are prerequisites. It was found that this object can be met by providing a poly(DL-lactide-ε-caprolactone) copolymer having a specific lactide content. Therefore, in the first aspect, the present invention relates to a polymeric material comprising poly(DL-lactide-ε-caprolactone) obtained by the copolymerization of DL-lactide and ε-caprolactone, having a lactide content of 51-75 mol %, preferably of 55-70 mol %, most preferably of 62-69 mol %.

The materials of the invention show excellent mechanical properties including stress-strain behavior, modulus and tensile strength, and excellent swelling behavior, when compared to the prior art poly(DL-lactide-co-ε-caprolactone) materials. Furthermore, the materials of the invention are completely amorphous. These properties make the materials of the invention very suitable for use as degradable device for medical purposes where both flexibility and mechanical strength are important characteristics, such as nerve guides, porous scaffolds, implants, artificial skin, artificial blood vessels, films and sheets for (tissue) adhesion prevention during and after surgical operations, but also for application in implantable or injectable long-term drug delivery systems.

The lactide (cyclic ester of two lactic acid molecules) is present in the copolymer as two lactic acid units.

The materials of the present invention combine flexibility with mechanical strength up to several weeks or months after implantation. Flexibility for example, is an important prerequisite for handling and shaping, whereas mechanical strength is important from a protective point of view. Scaffolds, for example, should provide sufficient mechanical support to allow tissue regeneration and maturation.

According to the present invention the lactide content in the copolymer is at least 51 mol %. Although copolymers with lactide contents below 51% are highly flexible, these materials have a modulus and glass transition temperature (Tg) that is too low to give the devices composed thereof sufficient mechanical strength. Moreover, the extent of swelling of these materials is too high for most biomedical applications, except possibly for sheets or wound dressings. For tubular implants or porous scaffolds for example, a low modulus and extensive swelling will lead to easier and undesired compression, deformation or total collapse and may consequently lead to insufficient protection of the newly formed tissue inside the tube.

Copolymers with a lactide content higher than 75% exhibit generally insufficient flexibility to be applied for the intended medical applications. In particular, nerve guides composed of copolymers with lactide contents higher than 75% cannot be sutured easily to the nerve stumps using an 8-0, 9-0 or 10-0 stitch, because of too high rigidity.

Therefore, the copolymers of the present invention have a lactide content of 51 to 75 mol %, preferably from 55-70 mol % and most preferably from 62-69 mol %. For example, nerve guides of 65:35 (85/15 L/D)lactide-ε-caprolactone that are used for peripheral nerve reconstruction have better mechanical properties (modulus and tensile strength) than nerve guides produced using the same monomers, but in a 50:50 monomer ratio (e.g. initial tensile strength of 40-50 MPa vs 2.5 MPa).

The known copolymers (with a low lactide content) were found to have a relatively low glass transition temperature (−12° C. vs 14° C. of the polymers according to the present invention). This low glass transition temperature affects the mechanical properties (easier compression) and swelling properties. Furthermore, polymerization conditions affect the polymer properties, as will be shown later.

Nerve guides with the indicated preferred lactide contents will retain better mechanical properties during nerve growth. The degree of swelling of these nerve guides can be very low, which prevents the risk of compression of the newly formed nerve tissue. Moreover, the flexibility of these polymers is favorable with respect to interaction with and response of the surrounding tissue The mechanical properties and the degradation behavior, in particular swelling, of the copolymer of the present invention may further be adjusted by choosing the ratio of the L-enantiomer to D-enantiomer of the lactide in the copolymer (L/D-ratio). Preferred copolymers, having excellent mechanical properties (particularly swelling behavior), are those having a lactide L/D-ratio (mol/mol) of 65/35 to 95/5, preferably 70/30 to 90/10, most preferably about 85/15. The swelling behavior of these preferred copolymers makes them particularly suitable for use as nerve guides. Copolymers having a L/D ratio of more than 95/5 may give rise to formation of crystalline material.

Conversely, a copolymer having a lactide ratio of the D-enantiomer to L-enantiomer of the lactide (D/L-ratio) in the above-mentioned preferred ranges may be used with similar advantage. For practical reasons, however, it is preferred to prepare the polymers having the indicated L/D-ratios rather than the D/L-ratios, since the L-enantiomer is less expensive.

In particular the stress-strain characteristics are considerably improved in the above-mentioned preferred ranges, as is illustrated in FIG. 1, showing, as an example, the mechanical properties of five nerve guides prepared in accordance with the present invention at synthesis temperatures of 110° C., 120° C. and 130° C., respectively. For comparison, the stress-strain behavior of a nerve guide of a copolymer with a 50:50 monomer ratio is shown (curve G), illustrating its inferior mechanical properties compared to those with a higher lactide content.

Furthermore, the L/D ratio has a pronounced effect on the swelling behavior, which is illustrated in FIG. 4. This figure clearly shows that swelling is reduced in nerve guides of a copolymer with a L/D ratio in the preferred range, compared to those of a copolymer with a L/D ratio equal to unity, while having the same lactide/caprolactone ratio.

The polymeric material according to the present invention may be produced by a conventional copolymerization reaction, as will be further illustrated hereinbelow. One of the synthesis conditions is the co-polymerization temperature. It was found that copolymers produced at 110° C. show somewhat better initial mechanical properties than copolymers with a similar composition and produced at 120° C.

A polymerization temperature lower than 110° C. will result in a lower conversion and a considerable longer polymerization time to obtain high conversions. Also, homogeneous mixing of the monomers is more difficult at lower temperatures (lactide melts at about 125° C.).

Although a high conversion generally will give a copolymer of a higher purity, the required purity can also be obtained easily by extraction of unreacted monomers using organic solvents.

The composition of the prepared copolymer may be determined using $^1$H-NMR at 300 MHz of solutions of the copolymer in deuterated chloroform. It is noted that the relative starting amounts of lactide and ε-caprolactone monomers used to synthesize the copolymer may differ significantly from the amount that is actually incorporated into the copolymer, as a result of incomplete conversion. The actual amount of monomers in the copolymers of the present invention (e.g. expressed as lactide content in the polymer, rather than relative amount of starting materials) can always be assessed by $^1$H-NMR at 300 MHz of solutions of the copolymer in deuterated chloroform.

The intrinsic viscosity may be used as a parameter which reflects the molecular weight, as will be explained in more detail below.

Preferred temperature ranges for the copolymerization reaction are from 100° C.-130° C., more preferably from 110-120° C. A higher polymerization temperature, generally results in a higher conversion but a lower molecular weight and shorter sequences of monomers in the copolymer.

The distribution of monomers in the copolymer may have a large effect on its properties. Since lactide and ε-caprolactone have different reactivities, the copolymer will have a more or less blocky structure. The length of the copolymer units consisting of one type of monomer (average sequence length, $L_{;Lac}$ and $L_{;Cap}$) is determined by the polymerisation conditions and monomer composition: higher polymerisation temperature, longer polymerization time and higher catalyst concentration result in smaller average sequence lengths (more transesterification takes place). A larger content of one of both monomers in the polymer will result in a larger average sequence length of this monomer.

Also, the L/D ratio of the lactide effects the average sequence lengths and therefore the other polymer properties (see results presented in Table 2).

The average lactide sequence length is generally higher in copolymers with a L/D ratio away from unity, such as L/D=85/15 (see e.g. Examples C and D below) than in similar copolymers with a L/D ratio equal or close to unity, such as L/D=50/50 (see e.g. Examples E and F below), when prepared under the same polymerisation conditions. Since the reactivity of L- and D-Lactide is the same, the average sequence length must be determined by the transesterification rate, which is lower in copolymers with L/D=85/15 than in copolymers with L/D=50/50, under the same conditions.

A suitable polymerization time is co-determined by the other polymerization conditions, in particular by the polymerization temperature and amount of catalyst used. Generally, the polymerization time ranges from 3-40 days, preferably from 5-13 days. Also, a longer polymerization time generally results in a higher conversion but a lower molecular weight and smaller sequences of monomers in the polymer. With a catalyst concentration of M/I=9000-12000 the preferred polymerisation time and temperature vary from a minimum of 3 days at 130° C. to a maximum of 40 days at 100° C. With lower catalyst concentration, the polymerisation time must be longer at the same temperature.

As mentioned before, as an example, nerve guides of 65:35 (85/15 L/D)lactide-ε-caprolactone that are used for peripheral nerve reconstruction have better mechanical properties than nerve guides with a 50:50 monomer ratio. Both the polymer composition and the method of preparation of the copolymer determine the mechanical properties of the nerve guides: a low lactide content (50%) and a very long polymerisation time of 22 days at 130° C. will result in a complete transesterification of the monomers, giving smaller average monomer sequence lengths. In an ideal random 50:50 copolymer the average lactide and caprolacton sequence length, $L_{;Lac}$ and $L_{;Cap}$, will be 4 and 2, respectively (H. R. Krichel-dorf and I. Kreiser, J. Macromol. Sci. Chem., A24 (11), 1345, (1987)). The monomer distribution in the prior art copolymer is completely random. Therefore, the small average lactide sequence length will result in poorer mechanical properties (e.g. modulus, tensile strength or toughness) of the 50:50 copolymer compared to those of the copolymers with a larger lactide content (and thus with a longer average lactide sequence length).

Ultimately, after prolonged polymerisation time and/or high polymerisation temperature, the monomer distribution will be completely random in all cases (all L/D ratios). However, of two copolymers with a similar average lactide sequence length, the one with a L/D ratio away from unity (e.g. 85/15) shows better mechanical properties than the one with a L/D ratio equal to unity. This proves that not only the size of the average monomer sequence lengths, but also the L-lactide content of the lactide sequence determines the mechanical properties. These results are confirmed by the data shown in Table 2.

Another important property of the copolymers of the present invention is the molecular weight and in particular the molecular weight distribution. The molecular weight (distribution) may e.g. be determined using gel permeation chromatography (GPC). More conveniently, however, the molecular weight is determined using a standardized intrinsic viscosity assay (ISO 1628-1). The value for the intrinsic viscosity ([ ]) thus obtained (expressed in dl/g) may be converted into the weight average molecular weight (Mw) by using the well-known Mark-Houwink expression: $[\ ]=KMw^a$, wherein K and a are polymer specific parameters. For lactide-ε-caprolactone copolymers having a lactide content of 45-55% the Mark-Houwink constants were determined experimentally using GPC: $K=3.303\ 10^{-3}$ and $a=0.548$. Similarly, the number-average molecular weight (Mn) may be correlated to the intrinsic viscosity: $[\ ]=1.019\ 10^{-3}\cdot Mn^{0.659}$, wherein the parameters were also determined using GPC. These values can also be applied to the copolymers of this invention with a higher lactide content.

Preferred polymeric materials of the present invention are those having a molecular weight that corresponds to an intrinsic viscosity, as assessed as described above, of more than 4 dl/g, preferably of more than 5 dl/g, more preferably of more than 5.5 dl/g. The molecular weight distribution or polydispersity (Mw/Mn), as determined using GPC) is preferably less than 1.8, more preferably less than 1.5.

The properties of the polymeric material, in particular the molecular weight (distribution), may be controlled by varying the amount of catalyst used in the polymerization reaction. Particularly good results are obtained by employing the catalyst in an amount such that the molar ratio of lactide and ε-caprolactone monomers to the catalyst (M/I) is from 1000-100000, preferably from 9000-12000. Lower M/I ratios (corresponding to a high catalyst concentration) generally result in faster polymerization and higher conversion, resulting in lower molecular weight and shorter sequences of monomers in the polymer. Higher M/I ratios generally give a higher molecular weight and longer sequences of monomers in the polymer. Suitable catalysts for this purpose are known to the skilled person. Particularly suitable are $Sn(oct)_2$ catalysts.

Of course, since the above-mentioned parameters (including polymerization time, polymerization temperature, initial monomer ratio and catalyst concentration) are correlated, optimal values for each of these parameters will differ per case. These optimal values can, however, easily be found in carrying out the invention, optionally by carrying out some routine experiments.

The copolymers of the present invention may be used in a variety of applications, in particular to provide the above-mentioned degradable devices for medical purposes, particularly to provide nerve guides. The polymers of the present invention can e.g. be processed into films, sheets, tubes, rods, plugs, microspheres or meshes, either solid or porous. Pores may vary from small and non-interconnected to large and interconnected. Microporous films (membranes) may also be produced of this material (e.g. having pore sizes as small as 5 μm).

Examples of other products that can be made of the materials of this invention are, biomedical drains; biomedical tubes for stenting purposes; biomedical sheets for intra-corporeal application such as an anti-adhesive sheet; biomedical sheets for topical use such as temporary wound care coverage or to prevent scarring; wound care foams; protective sheaths for needles and tubes which are introduced into the body; (micro)spheres for drug delivery; (micro)spheres, particles and plugs for embolization purposes; (micro)spheres for cosmetic surgical purposes, such as dermal augmentation, treatment of wrinkles and skin contour deficiencies; vascular prostheses; tissue engineering scaffolds, such as artificial skin or scaffolding plug for meniscus repair.

As will be illustrated in the examples below, the materials of the present invention have excellent properties, which include mechanical strength (tensile strength, modulus, strain at break, suture strength), thermal properties (glass transition temperature, crystallisation) and swelling (water uptake, increase of volume). Important for application as a nerve guide is the retention of its mechanical strength and compressibility during the time the new nerve has matured and retention of its dimensions (some swelling may be desirable for obtaining a permeable product, however, too much swelling results in obstruction of the lumen which will negatively affect nerve fiber regeneration).

EXAMPLES

Figure 1:
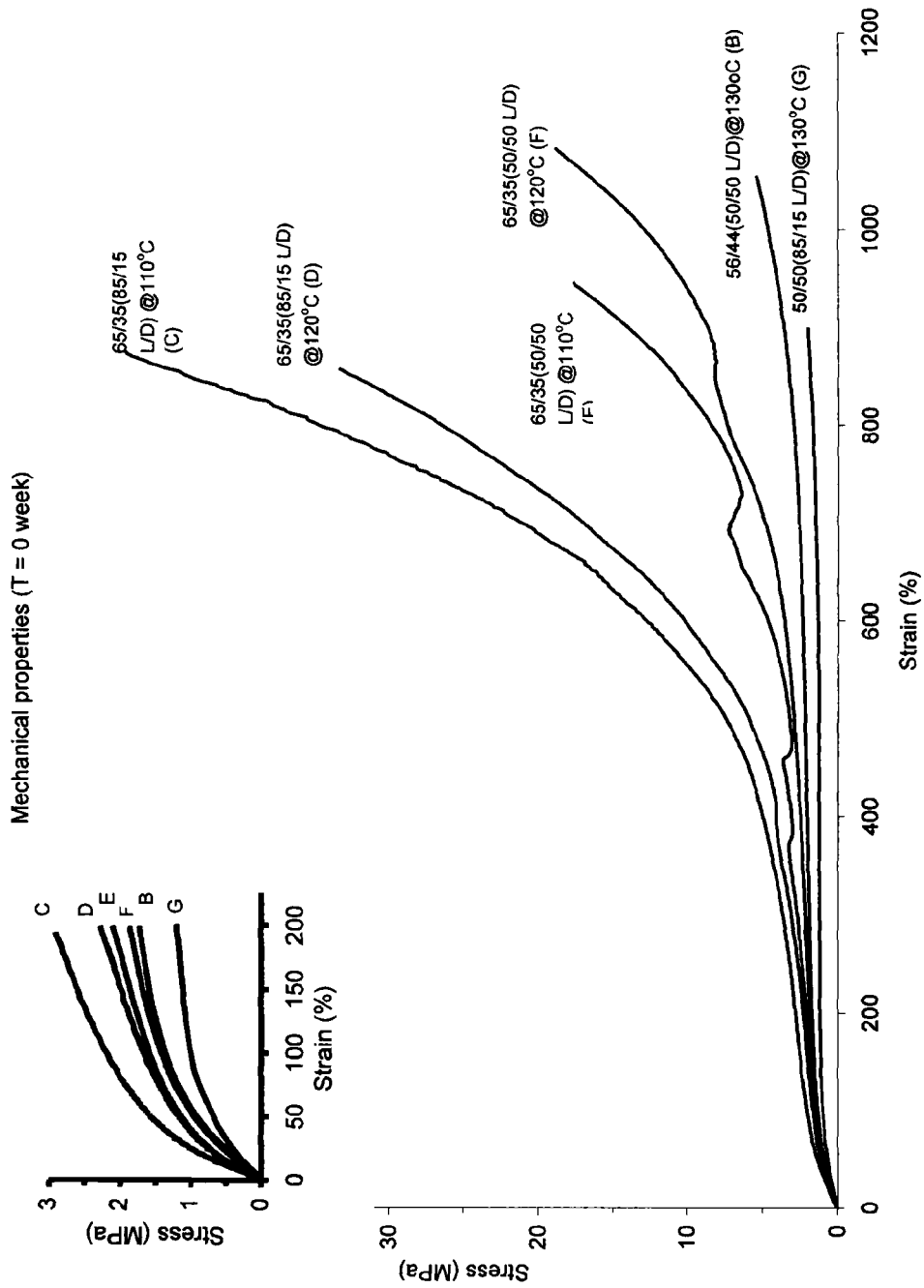
FIG. 1 shows the stress-strain relation of copolymers of DL-lactide and ε-caprolactone with different monomer composition and prepared at different polymerisation temperatures (using the notation [lactide/ε-caprolactone]([L-lactide]/[D-lactide])@[polymerization temperature/° C.]):
(C) 65/35(85/15 L/D)@110° C.;
(D) 65/35(85/15 L/D)@120° C.;
(E) 65/35(50/50 L/D)@110° C.;
(F) 65/35(50/50 L/D)@120° C.;
(B) 56/44(50/50 L/D)@130° C.;
(G) 50/50(85/15 L/D)@130° C.
The inset shows the stress-strain curves up to 200% strain.

The following notation is used to indicate the composition of the copolymers and their method of preparation: [lactide/ε-caprolactone molar ratio] ([L-lactide]/[D-lactide])@[polymerization temperature/° C.]).

Analysis Methods
Characterisation of Copolymers:
The following analysis methods were used in all examples, unless indicated otherwise.

The intrinsic viscosity was measured in chloroform at 25° C. using an Ubbelohde viscometer (according to ISO standard 1628-1).

The value for the intrinsic viscosity ([ ]) thus obtained (expressed in dl/g) is converted into the weight average molecular weight (Mw) by using the Mark-Houwink expression: $[\ ]=KMw^a$, wherein K and a are polymer specific parameters. The K and a values that were calculated for copolymers with 45-55% lactide have also been used for copolymers with higher lactide contents. In a similar way, the number average molecular weight, Mn, is calculated.

Monomer conversion, monomer distribution (average sequence length, $L;_{Lac}$ and $L;_{Cap}$) and copolymer composition were determined using $^1$H-NMR at 300 MHz in solutions in deuterated chloroform.

Characterisation of Nerve Guides:

Both initial properties and properties during the degradation study were measured on tubes prepared according to the method given in Example VII hereinbelow. Samples are dried to constant weight in vacuum at 40° C. before measurement, unless stated otherwise.

In vitro degradation studies were performed according to ISO/FDIS 15814 standards.

Intrinsic viscosities and copolymer composition of the tubes are determined by the methods described above.

Thermal properties were determined using a Perkin-Elmer DSC-7, 5-10 mg samples being heated at a rate of 10° C. per minute, cooled down at a rate of 40° C. per minute and heated again at a rate of 10° C. per minute.

The stress strain behavior was determined on an Instron 4301 tensile tester. The tubes are measured at room temperature at a crosshead speed of 10 mm/minute. The ultimate tensile strength, the stress at 250% strain, the elongation at break and the initial modulus were determined from these measurements. Tubes which were subjected to degradation were measured 'wet'; the loose water is removed by carefully drying with compressed air and by wiping with a tissue. The dimensions of the cross section of the tubes were measured with a microscope (Zeiss, type STEMI DV4) with a 32 magnification.

Swelling of the samples was calculated from the dimensional changes of the tubes, the dimensions being determined by the same method as used for the mechanical tests.

Purification and/or drying of monomers and glassware is according to previously published methods and is sufficient to obtain a polymer with the desired properties.

Example I

Copolymer A

DL-Lactide and L-Lactide (ratio 70:30) (Purac, the Netherlands) were introduced into a vessel under nitrogen atmosphere and the monomers were dried in vacuum at 45° C. for at least 8 hours. ϵ-Caprolactone (Acros, Belgium) is dried over $CaH_2$ and distilled under reduced pressure in a nitrogen atmosphere. The lactide and ϵ-caprolactone were added under a nitrogen flow in a glass ampoule in a monomer ratio of 50:50. The catalyst was added in an amount of $1·10^{-4}$ mole of catalyst per mole of monomer (M/I=$1·10^{-4}$). The ampoule was cooled in liquid nitrogen and sealed under vacuum ($10^{-6}$-$10^{-7}$ mbar). The ampoule was warmed to room temperature and then to 110° C. The contents were shaken until the mixture became homogeneous. The polymerization took place at 110° C. during 14 days.

The monomer conversion was 85%. The lactide content in the polymer was 67%. The intrinsic viscosity was 5.2 dl/g. The molecular weight, Mw, (measured by GPC) is 700000. The polydispersity, D, is 1.47.

Example II

Copolymer B

DL-Lactide (Purac, the Netherlands) was introduced into a vessel under nitrogen atmosphere and the monomer was dried in vacuum at 45° C. for at least 8 hours. ϵ-Caprolactone (Acros, Belgium) was dried over $CaH_2$ and distilled under reduced pressure in a nitrogen atmosphere. The lactide and ϵ-caprolactone were added under a nitrogen flow in a glass ampoule in a monomer ratio of 50:50. The catalyst was added in an amount of $1.2×10^{-4}$ mole of catalyst per mole of monomer. The ampoule was cooled in liquid nitrogen and sealed under vacuum ($10^{-6}$-$10^{-7}$ mbar). The ampoule was warmed to room temperature and then to 130° C. The contents were shaken until the mixture became homogeneous. The polymerization took place at 130° C. during 66 hours (3 days).

The monomer conversion was 88%. The lactide content in the polymer was 56%. The intrinsic viscosity was 4.2 dl/g. Precipitation of the polymer in ethanol (from a chloroform solution) yielded a polymer with an intrinsic viscosity of 5.5 dl/g.

The molecular weight, Mw, (measured by GPC) is 750000. The polydispersity, D, was 1.55.

Example III

Copolymer C

DL-Lactide and L-Lactide (ratio 70:30) (Purac, the Netherlands) were introduced into the reaction vessel under nitrogen atmosphere and were dried in vacuum at 45° C. for at least 8 hours. ϵ-caprolactone (Acros, Belgium) is dried over $CaH_2$ and distilled under reduced pressure in a nitrogen atmosphere.

Glass ampoules are covered inside with a teflon sheet (fluortec) and are dried in an oven during one night. ϵ-Caprolactone was added to the lactide in the vessel in a monomer ratio 62/38 mol/mol (lactide/ϵ-caprolactone). The catalyst was added in an amount of $1×10^{-4}$ mole of catalyst per mole of monomer. After 20 minutes of homogenisation at 120° C. the mixture was poured into the glass ampoules under nitrogen flow, after which the ampoules were closed with a stop. The ampoules were placed at 110° C. for 312 hours (13 days). The intrinsic viscosity was 6.2 dl/g. The monomer conversion was 95%. The lactide content in the polymer (calculated by NMR) was 65%.

Example IV

Copolymer D

The method of Example III was followed using a reaction temperature of 120° C. The polymerisation was carried out during 168 hours (7 days). The monomer conversion was 95%. The lactide content in the polymer was 65%. The intrinsic viscosity was 5.5 dl/g.

Example V

Copolymer E

The method of Example III was followed using L/D lactide in a ratio 50:50. The reaction temperature was 110° C. The polymerisation was carried out during 312 hours (13 days). The monomer conversion was 95%. The lactide content in the polymer was 65%. The intrinsic viscosity was 5.6 dl/g.

Example VI

Copolymer F

The method of Example III was followed using L/D lactide in a ratio 50:50. The reaction temperature was 120° C. The polymerisation was carried out during 168 hours (7 days). The monomer conversion was >96%. The lactide content in the polymer was 64%. The intrinsic viscosity was 5 dl/g.

The results of the copolymers A-F are summarized in Table 1.

Example VII

Preparation of Nerve Guides

Nerve guides were prepared from copolymers A-F, prepared as described above. To this end, for each copolymer a polymer solution in chloroform was dip-coated on mandrels with various diameters. After dipping, the mandrel was placed horizontally and the solvent was allowed to evaporate during 5 minutes while rotating. This procedure was repeated until the desired wall thickness was obtained. The mandrel with the copolymer layer was placed first in ethanol and after that in distilled water. The tubes were removed from the mandrel and were cut into the appropriate lengths. They were placed in ethanol, followed by vacuum drying at 40° C. in order to remove monomer- and low molecular weight residues and organic solvents. The properties of the thus obtained nerve guides are summarized in Table 2.

TABLE 1

Copolymer composition and polymerisation conditions

| Copolymer | lactide/ε-cap ratio in polymer | L/D- ratio of lactide | Polymerisation temperature | Polymerisation time [a] | Purification method (tubes) |
|---|---|---|---|---|---|
| A | 67/33 | 85/15 | 110° C. | 14 days/vacuum | Extraction with ethanol |
| B | 56/44 | 50/50 | 130° C. | 3 days/vacuum | Precipitated polymer |
| C | 65/35 | 85/15 | 110° C. | 13 days | Extraction with ethanol |
| D | 65/35 | 85/15 | 120° C. | 7 days | Extraction with ethanol |
| E | 65/35 | 50/50 | 110° C. | 13 days | Extraction with ethanol |
| F | 64/36 | 50/50 | 120° C. | 7 days | Extraction with ethanol |
| G [b] | 50/50 | 85/15 | 130° C. | 22 days | precipitated |

[a] The polymerization has been performed in vacuum where indicated, others were carried out under nitrogen atmosphere
[b] G is a prior art material. Method of preparation was previously published by Den Dunnen et al, J. Biomed. Mater. Res. 29 (1995) 757-766.

The thermal and mechanical properties and the monomer distribution were determined using the techniques described above. The results are given in Table 2.

TABLE 2

Thermal and mechanical properties and monomer distribution of nerve guides of copolymers with different monomer composition, prepared under various conditions.

| Code | Composition + Tpol | Stress at 250% [MPA] | Tensile strength [MPA] | E [MPA] | Strain at break [%] | Tg [° C.] | Llac[b] | Lcap[c] |
|---|---|---|---|---|---|---|---|---|
| A | 67/33(85/15 L/D)@110° C. | 3.0 | 40.0 | 4.5-5.0 | 900 | 17.7 | 8.9 | 2.0 |
| C | 65/35(85/15 L/D)@110° C. | 3.0 | 38.3 | 4.5 | 835 | 14.6 | 9.2 | 2.5 |
| D | 65/35(85/15 L/D)@120° C. | 2.8 | 32.2 | 4.1 | 833 | 14.4 | 8.0 | 2.2 |
| E | 65/35(50/50 L/D)@110° C. | 2.2 | 15.2 | 3.5 | 910 | 11.7 | 8.1 | 2.2 |
| F | 65/35(50/50 L/D)@120° C. | 1.9 | 17.2 | 2.5 | 1080 | 11.5 | 7.0 | 1.9 |
| B | 56/44(50/50 L/D)@130° C. | 1.8 | 4.1 | 2.4 | 925 | 3.8 | 5.5 | 2.2 |
| G | 50/50(85/15 L/D)@130° C. | 1.3 | 2.5 | 1.5 | 900 | −12.0 | 4.0 | 2.0 |

[a] G is a prior art material. Part of the properties of (G) were previously published by Den Dunnen et al, J. Biomed. Mater. Res. 29 (1995) 757-766.
[b] $L;_{Lac}$: length of the copolymer units consisting of lactide monomers (average sequence length).
[c] $L;_{Cap}$: length of the copolymer units consisting of caprolactone monomers (average sequence length).

RESULTS AND DISCUSSION

FIG. 1 shows the effect of copolymer composition on the initial stress-strain relation of nerve guides of poly(DL-Lactide-ε-caprolactone) with different monomer composition (copolymers C (65/35-85/15@110), D (65/35-85/15@120), E (65/35-50/50@110), F (65/35-50/50@120), B (56/44-50/50@130)) and G (50/50-85/15@130)). It follows clearly from the results in Table 2 and FIG. 1 that upon decrease of the lactide content, the mechanical properties are reduced. However, the initial properties of all tubes A-F make them suitable to be applied for nerve guides or other medical devices. Furthermore, the copolymers with a 85/15 L/D ratio have better initial mechanical properties than their 50/50 analogues, if prepared under the same conditions. They also have higher values of the Tg. Moreover, the lower the polymerization temperature, the better the mechanical properties. The polymerisation temperature has only a minor effect on the value of Tg.

Figure 2:
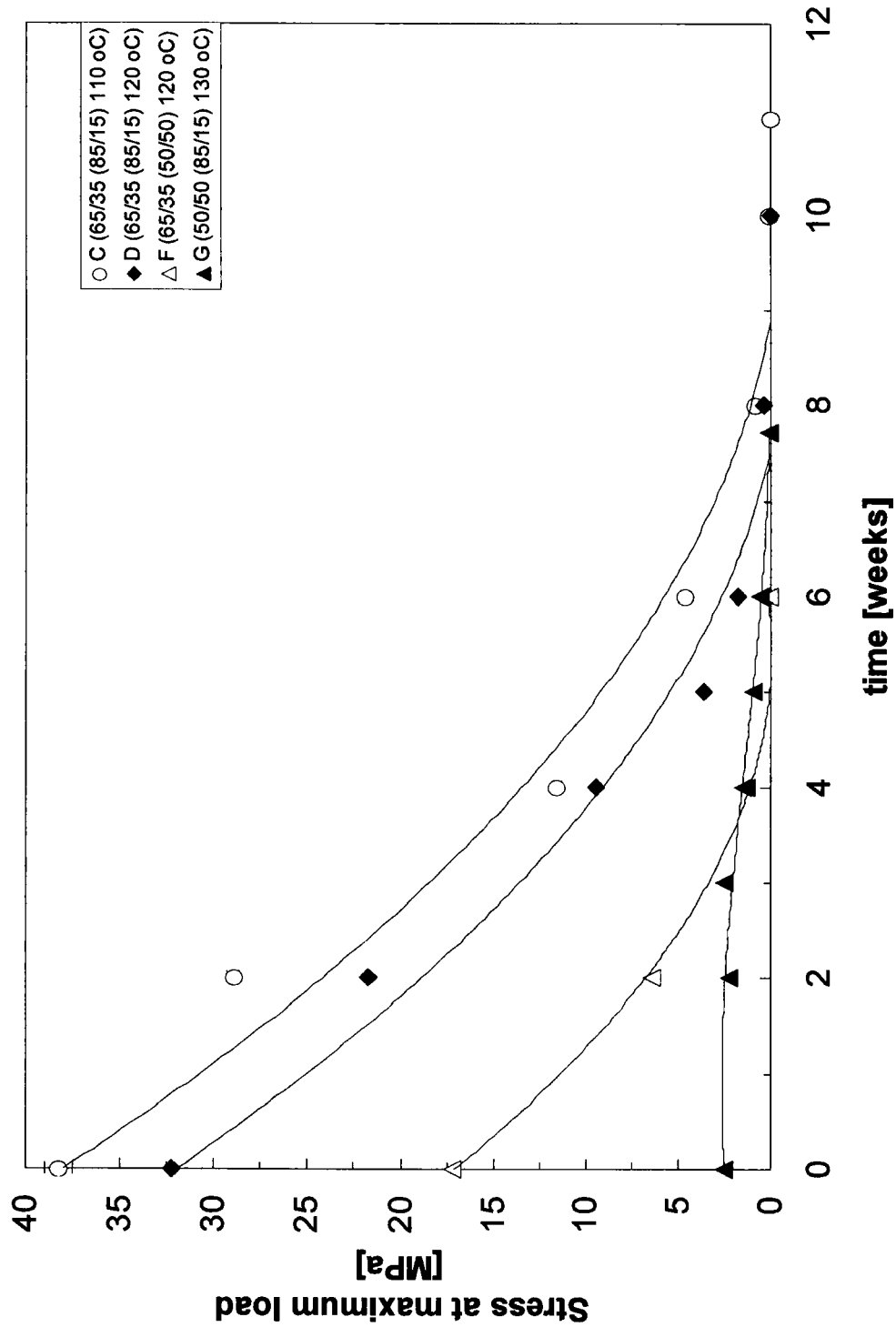
FIG. 2 shows the tensile strength (stress at break) of poly (DL-lactide-ε-caprolactone) copolymer test samples as a function of time (Δ (open triangles): F; ♦ (closed diamonds): D; and ○ (open circles): C in vitro measurements using copolymers of indicated composition (notation as in FIG. 1), L=30 mm, outer diameter=2.2 mm, wall thickness=0.30-0.40 mm) and bars (▲ (closed triangles): G, in vivo measurements, subcutaneously implanted bars of 3×3×15 mm).

FIG. 2 shows the stress at break (tensile strength) of poly (DL-lactide-ε-caprolactone) nerve guides with 65/35 copolymer ratio as a function of degradation time (in vitro experiments, phosphate buffer pH 7.5, 37° C., 2 batches, N=3 per batch). Moreover, the results of tubes of copolymer G (50/50 monomer ratio) are depicted for comparison.

Figure 3:
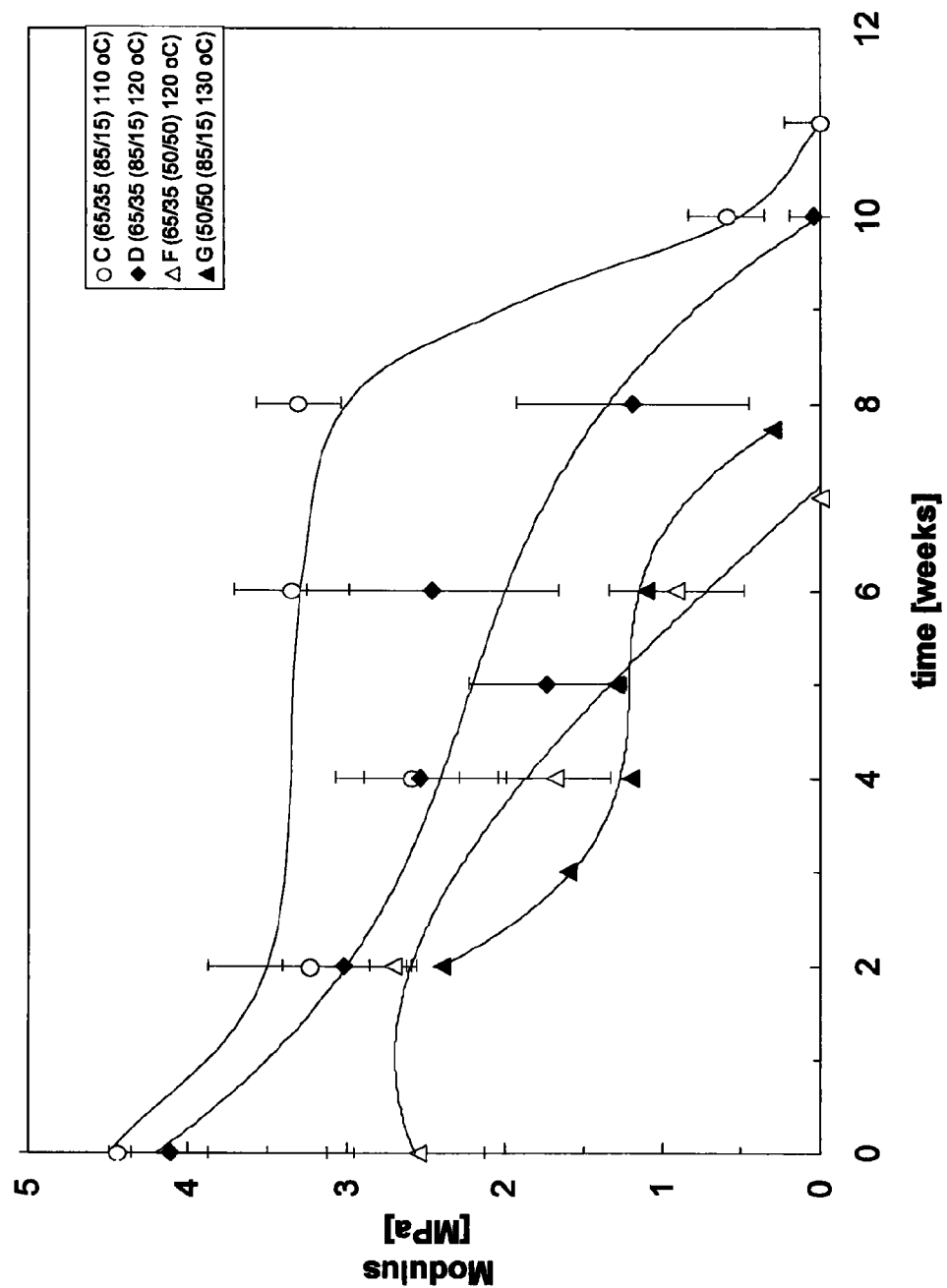
FIG. 3 shows the elastic modulus (E) of poly(DL-lactide-ε-caprolactone) copolymer test samples, as calculated from the stress—strain curves at low elongation, as a function of time (for symbol legend see FIG. 2).

FIG. 3 shows the change in Elastic Modulus of the nerve guides described under FIG. 2 (C, D, F and G) over time under the same conditions.

From these figures it follows that the copolymers of the invention display improved mechanical properties for application in medical devices such as artificial bioresorbable nerve guides, as compared to the prior art material.

Figure 4:
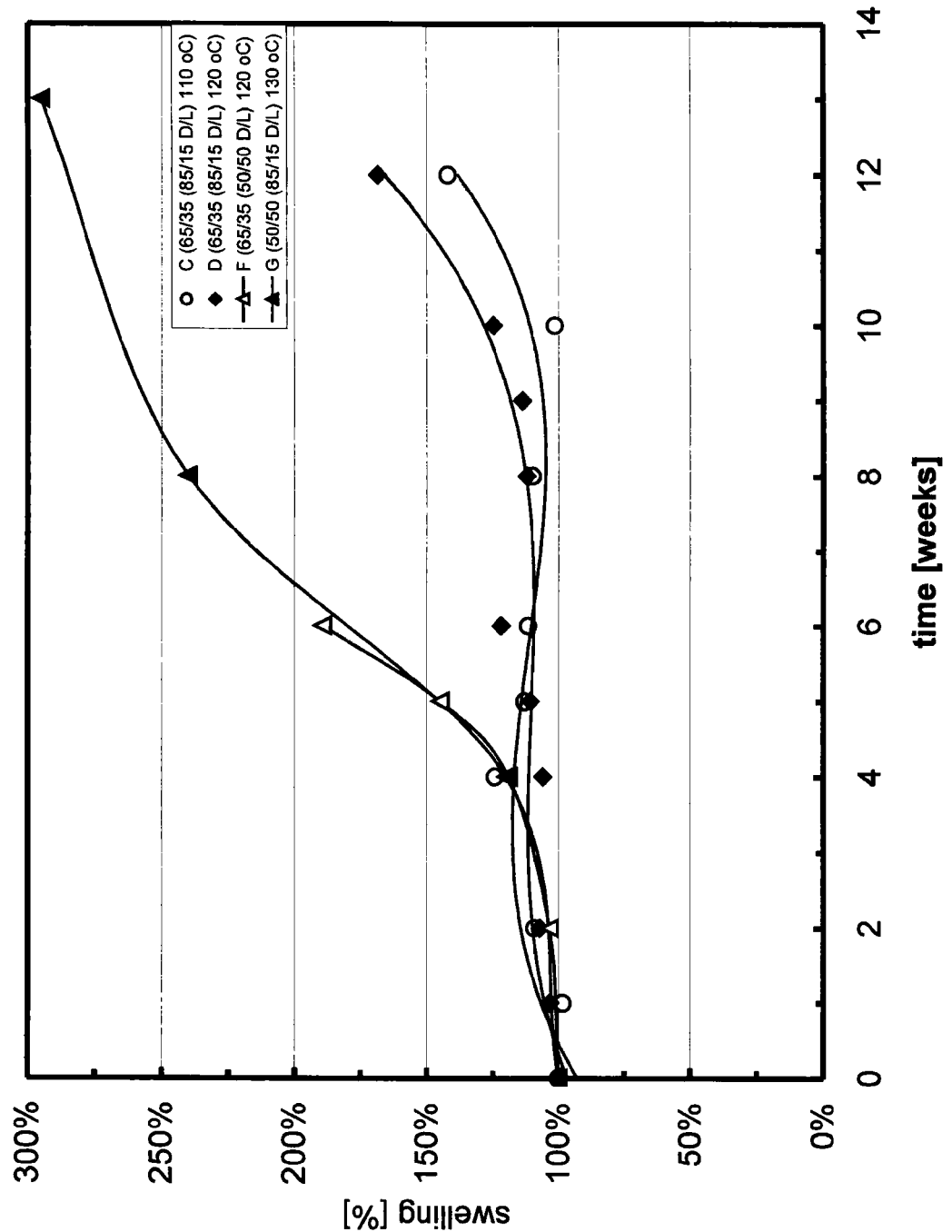
FIG. 4 shows the swelling of poly(DL-lactide-ε-caprolactone) copolymers as calculated from the volume increase of nerve guide samples (for symbol legend see FIG. 2).

FIG. 4 shows the swelling of the nerve guides made from copolymers C, D, F and G over time under the same conditions. Clearly it is shown that both lactide content and L/D ratio largely affect swelling of the nerve guides.

What is claimed:

1. Polymeric material comprising a poly(DL-lactide-co-ε-caprolactone) copolymer obtained by the copolymerization of DL-lactide and ε-caprolactone, which copolymer has a lactide content of 51-75 mol % and wherein the fraction of D-enantiomer or L-enantiomer of the lactide is from 65-95 mol %.

2. Polymeric material according to claim 1, having a polydispersity (Mw/Mn) of less than 1.8.

3. Polymeric material according to claim 1, having an intrinsic viscosity of more than 4 dl/g.

4. Polymeric material according to claim 1, which is obtained by carrying out said polymerization at a temperature of 100° C.-130° C.

5. Polymeric material according to claim 1, which is obtained by carrying out said polymerization during a period of 3-40 days, wherein the temperature is linearly depending on the polymerization time from the interval: 130° C. (at 3 days) to 100° C. (at 40 days).

6. Polymeric material according to claim 1, which is obtained by carrying out said polymerization using a catalyst in an amount such that the molar ratio of lactide and ε-caprolactone monomers to said catalyst (M/I) is from 1000-100000.

7. Article for medical application, comprising a polymeric material according to claim 1.

8. Article according to claim 7, which is selected from the group consisting of biomedical drains; biomedical tubes for stenting purposes; biomedical sheets for intra-corporeal application; biomedical sheets for topical use; wound care foams; protective sheaths for needles and tubes which are introduced into the body; (micro)spheres for drug delivery; (micro)spheres, particles and plugs for embolization purposes; (micro)spheres for cosmetic surgical purposes; vascular prostheses; tissue engineering scaffolds.

9. Nerve guide according to claim 7.

10. The polymeric material of claim 1 wherein the copolymer has a lactide content of 55-70 mol %.

11. The polymeric material of claim 1 wherein the copolymer has a lactide content of 62-69 mol %.

12. The polymeric material of claim 1 wherein the fraction of D-enantiomer or L-enantiomer of the lactide is from 70-90 mol %.

13. The polymeric material of claim 1 wherein the fraction of L-enantiomer of the lactide is about 85 mol %.

14. Polymeric material according to claim 1, having a polydispersity (Mw/Mn) of less than 1.5.

15. Polymeric material according to claim 1, having an intrinsic viscosity of more than 5 dl/g.

16. Polymeric material according to claim 1, having an intrinsic viscosity of more than 5.5 dl/g.

17. Polymeric material according to claim 1, which is obtained by carrying out said polymerization at a temperature of 110-120° C.

18. Polymeric material according to claim 1, which is obtained by carrying out said polymerization using a $Sn(oct)_2$ catalyst, in an amount such that the molar ratio of lactide and ε-caprolactone monomers to said catalyst (M/I) is from 1000-100000.

19. Polymeric material according to claim 1, which is obtained by carrying out said polymerization using a $Sn(oct)_2$ catalyst, in an amount such that the molar ratio of lactide and ε-caprolactone monomers to said catalyst (M/I) is from 9000-12000.

20. Polymeric material comprising a poly(DL-lactide-co-ε-caprolactone) copolymer obtained by the copolymerization of DL-lactide and ε-caprolactone, which copolymer has a lactide content of 62-69 mol % and wherein the fraction of L-enantiomer of the lactide is about 85 mol %.

* * * * *